US005487987A

United States Patent [19]
Frost et al.

[11] Patent Number: 5,487,987
[45] Date of Patent: * Jan. 30, 1996

[54] SYNTHESIS OF ADIPIC ACID FROM BIOMASS-DERIVED CARBON SOURCES

[75] Inventors: John W. Frost; Karen M. Draths, both of West Lafayette, Ind.

[73] Assignee: Purdue Research Foundation, West Lafayette, Ind.

[ * ] Notice: The portion of the term of this patent subsequent to Dec. 1, 2009, has been disclaimed.

[21] Appl. No.: 122,920

[22] Filed: Sep. 16, 1993

[51] Int. Cl.$^6$ ..................................................... C12P 7/44
[52] U.S. Cl. .................... 435/142; 435/175; 435/189; 435/232; 435/320.1; 435/252.3; 435/252.33; 435/172.3; 536/23.2; 536/23.7; 935/60; 935/27; 935/72
[58] Field of Search .................................... 435/142, 175, 435/189, 232, 320.1, 252.3, 252.33, 172.3; 536/23.2, 23.7; 935/60, 61, 72, 73, 14

[56] References Cited

U.S. PATENT DOCUMENTS

| | | | |
|---|---|---|---|
| 3,912,586 | 10/1975 | Kaneyuki et al. | 435/142 |
| 3,970,522 | 7/1976 | Sasajima et al. | 435/105 |
| 4,355,107 | 10/1982 | Maxwell | 435/142 |
| 4,400,468 | 8/1983 | Faber | 435/142 |
| 4,681,852 | 7/1987 | Tribe | 435/109 |
| 4,753,883 | 6/1988 | Backman et al. | 435/232 |
| 4,908,312 | 3/1990 | Ozaki et al. | 435/108 |
| 4,968,612 | 11/1990 | Hsieh | 435/142 |
| 5,017,481 | 5/1991 | Matsui et al. | 435/108 |
| 5,168,056 | 12/1992 | Frost | 435/172.3 |
| 5,272,073 | 12/1993 | Frost et al. | 435/155 |

OTHER PUBLICATIONS

Asahi Kasei Kogyo K.K., "Manufacture of Adipic Acid by Biotechnology", Bio Industry, vol. 8, No. 10, pp. 671–678, 1991.
A. J. Pittard, "Biosynthesis of the Aromatic Amino Acids", in *Escherichia coli & Salmonella typhimurium*, Editor in Chief: F. C. Neidhardt, American Soc. for Microbiology, Washington, pp. 368–394, 1987.
K. M. Herrmann et al., "The Common Aromatic Biosynthesis Pathway" in Amino Acids: Biosynthesis and Genetic Regulation, Addison–Wesley Reading, pp. 301–376, 1983.
K. M. Draths et al. "Synthesis Using Plasmid–Based Biocatalysis: Plasmid Assembly and 3–Deoxy–arabino–heptulosonate Production", JACS, vol. 112, pp. 1657–1659, 1990.
Wen Hsiung Liu and Tso Lin Cheng, "Microbial Production of cis–cis–muconic acid from Benzoic Acid", Chemical Abstracts, vol. 116, p. 653, 1992.
K. M. Draths & J. S. Frost, "Genomic Direction of Synthesis During Plasmid–Based Biocatalysis", JACS, 1990, vol. 112, p. 9630.
Stu Borman, "New biosynthetic route to catechol discovered", C&EN, p. 26, Jan. 6, 1992.
K. M. Draths and J. W. Frost, "Conversion of D–Glucose into Catechol: The Not–So–Common Pathway of Aromatic Biosynthesis", J. Am. Chem. Soc., vol. 113, No. 25, pp. 9361–9363, 1991.
David Brewster, Robin S. Jones and Dennis V. Parke, "Aromatization of Shikimic Acid in the Rat and the Role of Gastrointestinal Micro–Organisms", 562nd Meeting of Biochemical Society Transactions; pp. 518–521, 1976.
David Brewster, Robin S. Jones and Dennis V. Parke, "The Metabolism of Shikimate in the Rat", Biochem J., vol. 170, pp. 257–264, 1978.
Neil C. Bruce and Ronald B. Cain, "Hydroaromatic Metabolism in *Rhodococcus Rhodochous*: Purification and Characterisation of its NAD–dependent Quinate Dehydrogenase"; Archives of Microbiology, vol. 154 pp. 179–186, 1990.
John W. Frost, Judith L. Bender, James T. Kadonaga and Jeremy R. Knowles, "Dehydroquinate Synthase from *Escherichia coli*: Purification, Cloning, and Construction of Overproducers of the Enzyme", Biochemistry, vol. 23, pp. 4470–4475, 1984.
K. M. Draths and J. W. Frost, "Genomic Direction of Synthesis during Plasmid–Based Biocatalysis", Journal of the American Chemical Society, vol. 112, pp. 9630–9632, 1990.
J. L. Canovas, M. L. Whellis, and R. Y. Stanier, "Regulation of the Enzymes of the β–Ketoadipate Pathway in *Moraxella calcoacetica*—The Role of Protocatechuate as Inducer", European Journal of Biochemistry, vol. 3, pp. 293–304, 1968.
W. M. Ingledew, M. Elena F. Tresguerres and J. L. Canovas, "Regulation of the Enyzmes of the Hydroaromatic Pathway in *Acinetobacter calco–aceticus*", The Journal of General Microbiology, vol. 68, pp. 273–282, 1971.
J. Elena F. Tresguerres, W. M. Ingledew, and J. L. Canovas, "Potential Competition for 5–Dehydroshikimate between the Aromatic Biosynthetic Route and the Catabolic Hydroaromatic Pathway", Arch. Mikrobiol. vol. 82, pp. 111–119, 1972.
Heather K. Lamb, Clive R. Bagshaw, and Alastair R. Hawkins, "In vivo overproduction of the pentafunctional arom polypeptide in *Aspergillus nidulans* affects metabolic flux in the quinate pathway", MGG, vol. 227, pp. 187–196, 1991.

(List continued on next page.)

*Primary Examiner*—Christopher S. F. Low
*Attorney, Agent, or Firm*—Barnes & Thornburg

[57] ABSTRACT

A method is provided for producing adipic acid. The method comprises the steps of culturing a cell transformant capable of converting a carbon source to catechol for a period of time sufficient to convert said carbon source to catechol, biocatalytically converting the catechol to cis, cis-muconic acid using catechol 1,2-dioxygenase, and hydrogenating the cis, cis-muconic acid to produce adipic acid.

Also provided is a heterologous transformant of the host cell having an endangeous common pathway of aromatic amino acid biosynthesis. The heterologous transformant is characterized by the constitutive expression of structural genes encoding 3-dehydroshikimate dehydratase, protocatechuate decarboxylase, and catechol 1,2-dioxygenase.

3 Claims, 4 Drawing Sheets

OTHER PUBLICATIONS

R. B. Cain, "The Regulation of Enzymes of Aromatic–Ring Fission in Fungi: Organisms using only the Protocatechuate Pathway", Biochemical Journal vol. 114(4) p. 76, 1969.

R. S. Chaleff, "The Inducible Quinate–Shikimate Catabolic Pathway in *Neurospora Crassa:* Genetic Organization", Journal of General Microbiology, vol. 81 pp. 337–355, 1974.

C. Ratledge, "The Production of an N–Acylanthranilic Acid From Shikimic Acid and the Effect of Iron Deficiency on the Biosynthesis of other Aromatic Compounds By *Aerobacter aerogenes*", Biochimica Et Biophysica Acta, vol. 141, pp. 55–63, 1967.

J. C. Patel and D. J. W. Grant, "The Formation of Phenol in the Degradation of p–hydroxybenzoic acid by *Klebsiella aerogenes (Aerobacter aerogenes)*", Antonie van Leeuwenhoek, vol. 35, pp. 53–64, 1969.

A. J. Pittard, F. Gibson, and C. H. Doy, "A Possible Relationship Between The Formation of o–Dihydric Phenols and Tryptophan Biosynthesis By *Aerobacter aerogenes*", Biochimica ET Biophysica Acta, vol. 57, pp. 290–298, 1962.

A. J. Pittard, F. Gibson and C. H. Doy, "Phenolic Compounds Accumulated By Washed Cell Suspensions of a Tryptophan Auxotroph of *Aerobacter aerogenes*", Biochim, Biophys, Acta, vol. 49, pp. 485–494, 1961.

D. J. W. Grant, "The Oxidative Degradation of Benzoate and Catechol by *Klebsiella aerogenes (Aerobacter aerogenes)*", Antonie van Leeuwenhock, vol. 36, pp. 161–177, 1970.

D. B. Norris and P. W. Trudgill, "The Metabolism of Cyclohexanol", Biochem, vol. 121, pp. 363–370, 1971.

A. Donoghue and Peter W. Trudgill, "The Metabolism of Cyclohexanol by *Acinetobacter* NCIB 9871", Eur. J. Bochem., vol. 60, pp. 1–7, 1975.

John Casey, Roy Thomas Dobb and Roger Jeffcoat, "Preparation of Dicarboxylic Acids with Candida Cloacae", Chemical Abstracts, vol. 112, p. 501, 1990.

Kokai Tokkyo Koho, "Production of Dicarboxylic Acids by Fermentation", Chemical Abstracts, vol. 97 (1982).

Kokai Tokkyo Koho, "Adipic Acid Production by Nocardia", Chemical Abstracts, vol. 99 (1983).

SYNTHESIS OF ADIPIC ACID FROM BIOMASS-DERIVED CARBON SOURCES

BACKGROUND AND SUMMARY OF THE INVENTION

This invention relates to the production of adipic acid and precursors thereof by the conversion of biomass-derived carbon sources. More particularly this invention is directed to the biocatalytic conversion of glucose and other sugars capable of being used in the biosynthesis of aromatic amino acids to adipic acid via 3-dehydroshikimate dehydratase, protocatechuate decarboxylase, and catechol 1, 2 dioxygenase, followed by hydrogenation.

Annual world-wide production of adipic acid in 1989 was estimated at 4.2 billion pounds. With U.S. production at 1.75 billion pounds in 1992, adipic acid consistently ranks as one of the top fifty chemicals produced domestically. Nearly 90% of domestic adipic acid is used to produce nylon-6,6. Other uses of adipic acid include production of lubricants and plasticizers, and as a food acidulant.

The dominant industrial process for synthesizing adipic acid employs initial air oxidation of cyclohexane to yield a mixture of cyclohexanone (ketone) and cyclohexanol (alcohol), which is designated KA. Hydrogenation of phenol to yield KA is also used commercially, although this process accounts for just 2% of all adipic acid production. KA produced via both methods is oxidized with nitric acid to produce adipic acid. Reduced nitrogen oxides including $NO_2$, NO, and $N_2O$ are produced as by-products and are recycled back to nitric acid at varying levels.

These processes are not entirely desirable due to their heavy reliance upon environmentally sensitive feedstocks, and their propensity to yield undesirable by-products. Cyclohexane is derived from benzene, a known carcinogen which is obtained from nonrenewable fossil fuels. Cyclohexane itself is currently under investigation as a toxic material. Moreover, nitric acid oxidation has been reported to account for 10% of the global increase in atmospheric nitrous oxide. Nitrous oxide has been implicated in the depletion of the ozone layer.

Extensive research has been directed at alternative processes of adipic acid synthesis, though none have been commercialized. Reactions involving cobalt-catalyzed air oxidation of cyclohexane directly to adipic acid or oxidation of cyclohexane with ozone have been examined as methods which avoid intermediate production of KA. Here again, the use of cyclohexane and phenol as feedstocks is undesirable from an environmental standpoint.

Research has also focused on synthesis of adipic acid from alternative feedstocks. Significant attention has been directed at carbonylation of butadiene. More recently, a method of dimerizing methyl acrylates was reported, opening up the possibility of adipic acid synthesis from C-3 feedstocks.

Exploitation of biological systems has also been examined. A strain of *Pseudomonas putida* has been developed which catalyzes conversion of toluene to cis, cis-muconic acid, which can be hydrogenated to afford adipic acid. However, this method is similar to traditional chemical technology in that it begins with toluene, an environmentally undesirable feedstock. Strains of Acinetobacter and Norcardia have been reported which, when grown on cyclohexanol as the sole source of carbon, produce adipic acid as an intermediate in the metabolic pathway.

Alternatively, strains of *Norcardia* and *Pichia carboniferus* have been reported which synthesize adipic acid from diaminododecane and myristic acid, respectively. However, processes based upon these strains are commercially unattractive because starting materials are particularly expensive. Moreover, the biochemical reactions and the induction of enzymatic activities have not been clearly elaborated.

One process combining elements of biocatalysis and chemistry entails the multi-step chemical conversion of biomass into 1,6-hexanediol, which is then oxidized to adipic acid by *Gluconobacter oxydans*. While this process relies on inexpensive starting materials, it requires multiple chemical conversions which are carried out at elevated temperatures (100° C.–350° C.) and pressures (up to 20,000 psi) and employs multiple metal catalysts including copper chromite.

It would be desirable to provide a synthesis route for adipic acid which not only avoids reliance on environmentally sensitive starting materials but also makes efficient use of inexpensive, renewable resources. It would further be desirable to provide a synthesis route for adipic acid which avoids the need for significant energy inputs and which minimizes the formation of toxic by-products.

The present invention provides methods for the microbial biosynthesis of adipic acid from readily available carbon sources capable of biocatalytic conversion to erythrose 4-phosphate (E4P) and phosphoenolpyruvate (PEP) in microorganisms having a common pathway of aromatic amino acid biosynthesis. One preferred carbon source is D-glucose. Advantageously, D-glucose, and other carbon sources useable in connection with the present invention, are non-toxic. Furthermore, they are renewable resources derived from starch, cellulose, and sugars found in corn, sugar cane, sugar beets, wood pulp, and other biomass resources.

Host microbial organisms suitable for carrying out the present invention belong to genera possessing an endogenous common pathway of aromatic amino acid biosynthesis. Preferred host organisms are mutant strains of *Escherichia coli* genetically engineered to express selected genes endogenous to *Klebsiella pneumoniae* and *Acinetobacter calcoaceticus*. One preferred *E. coli* mutant for use in this invention is *E. coli* AB2834, an auxotrophic mutant which is unable to catalyze the conversion of 3-dehydroshikimate (DHS), an intermediate along the common pathway, into shikimic acid and thereafter into chorismate due to a mutation in the aroE locus which encodes shikimate dehydrogenase.

The common pathway of aromatic amino acid biosynthesis produces the aromatic amino acids, phenylalanine, tyrosine, and tryptophan in bacteria and plants. The common pathway ends in the branch point molecule chorismate, which is subsequently converted into phenylalanine, tyrosine, and tryptophan by three separate terminal pathways.

Approaches for increasing the efficiency of production of the common pathway have been described in U.S. Pat. No. 5,168,056 (issued Dec. 1, 1992) and in U.S. patent application Ser. No. 07/994,194, filed Dec. 21, 1992, the disclosures of which are hereby expressly incorporated by reference.

In using the genetically engineered, mutant host organisms to produce adipic acid according to this invention, carbon flow directed into aromatic amino acid biosynthesis proceeds along the common pathway to yield elevated intracellular levels of the DHS intermediate, which accumulate due to a mutation along the common pathway of aromatic amino acid biosynthesis which prevents the conversion of DHS to chorismate. The DHS intermediate serves as a substrate for the enzyme 3-dehydroshikimate dehydratase to produce protocatechuate. Protocatechuate is thereafter converted to catechol with protocatechuate decarboxylase. Catechol is in turn converted to cis, cis-muconic acid by the action of catechol 1, 2-dioxygenase. Synthesized cis, cis-muconic acid accumulates extracellularly and can be separated from the cells by centrifugation. Cis, cis-muconic acid is thereafter directly hydrogenated to yield adipic acid.

Preferably, the enzymes catalyzing the biosynthesis of cis, cis-muconic acid are expressed in the host cell with recombinant DNA comprising genes encoding the enzymes under control of a constitutive promoter. Carbon flow is thereby forced away from the common pathway, into the divergent pathway to produce cis, cis-muconic acid.

In contrast to known multi-step, energy-intensive conversion processes, the processes of this invention rely on a single-step microbial conversion at relatively low temperature (e.g. about 37° C.) and atmospheric pressure, followed by a single chemical transformation performed at ambient temperatures at mild pressures (50 psi) with a platinum catalyst. Moreover, a 90% or higher conversion of the biosynthesized cis, cis-muconic acid to adipic acid can be achieved.

In one preferred embodiment using the host strain E. coli AB2834, DHS intracellular concentrations are increased due to a mutation in a gene (aroE) which encodes shikimate dehydrogenase. DHS is transformed to catechol along a divergent pathway enabled by transformation of the host cell with expressible genetic fragments encoding DHS dehydratase and protocatechuate decarboxylase and with genes encoding for enzymes which commit an increased amount of carbon to the common pathway of aromatic amino acid biosynthesis. Further transformation of the host cell with expressible genetic fragments encoding catechol 1, 2-dioxygenase enables the biocatalytic conversion of catechol to cis, cis-muconic acid, which, upon separation from the cells, is directly hydrogenated over 10% platinum on carbon at 50 psi hydrogen pressure for three hours at room temperature to generate adipic acid. Analysis of culture supernatants of recombinant mutants of this invention using nuclear magnetic resonance spectroscopy (NMR) demonstrates that adipic acid is the primary product. A 90% conversion of cis, cis-muconate into adipic acid can be achieved.

Additional objects, features, and advantages of the invention will become apparent to those skilled in the art upon consideration of the following detailed description of preferred embodiments exemplifying the best mode of carrying out the invention as presently perceived.

DETAILED DESCRIPTION OF THE INVENTION

In accordance with this invention there is provided a method for producing adipic acid from biomass-derived carbon sources capable of being used by a host cell having a common pathway of aromatic amino acid biosynthesis. In one preferred embodiment, the method comprises the steps of culturing the host cell in the carbon source to produce cis, cis-muconic acid, and reducing the cis, cis-muconic acid to produce adipic acid.

Figure 1A:
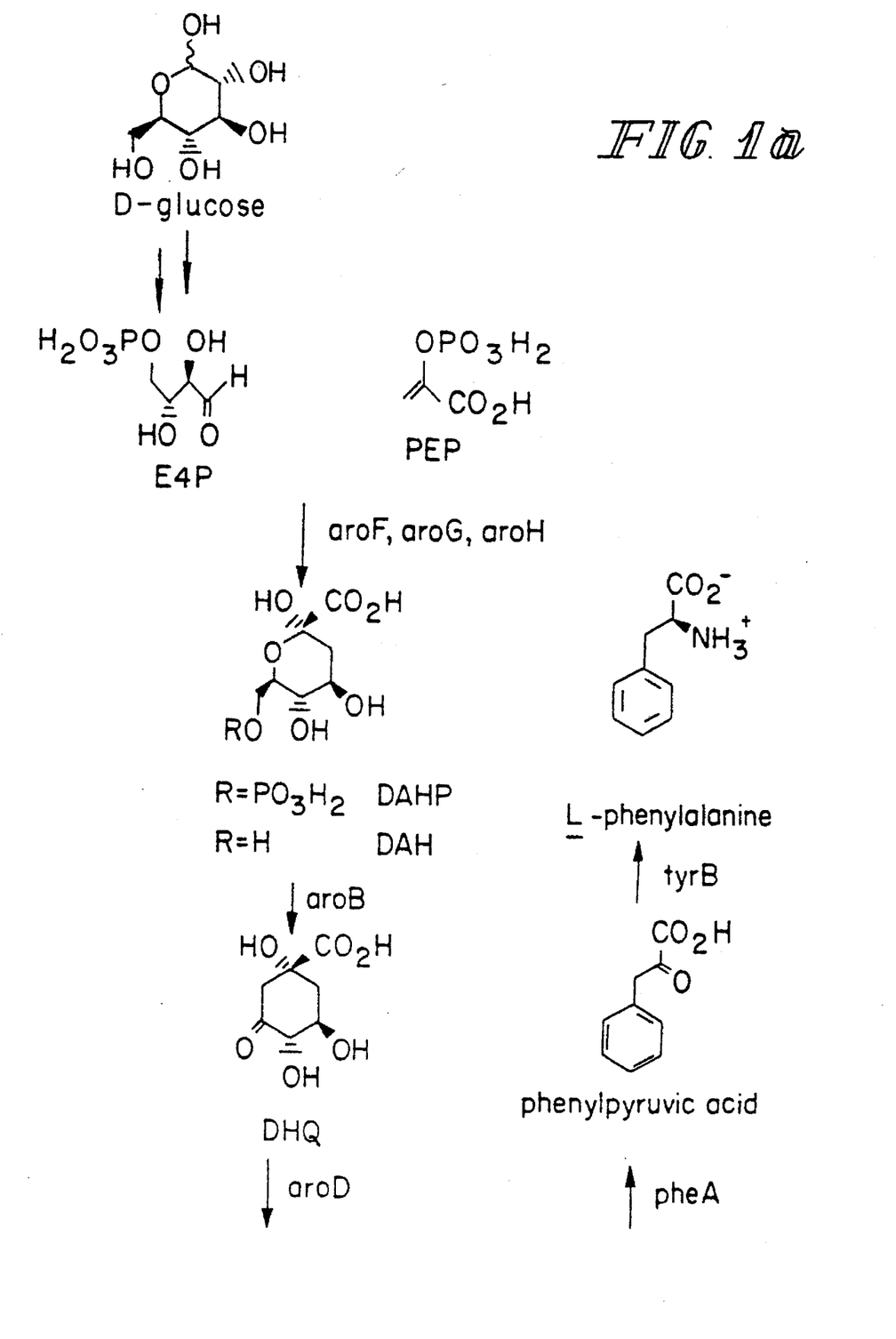
FIG. 1 illustrates the common pathway of aromatic amino acid biosynthesis and the divergent pathway synthesizing adipic acid from 3-dehydroshikimate.
Figure 1B:
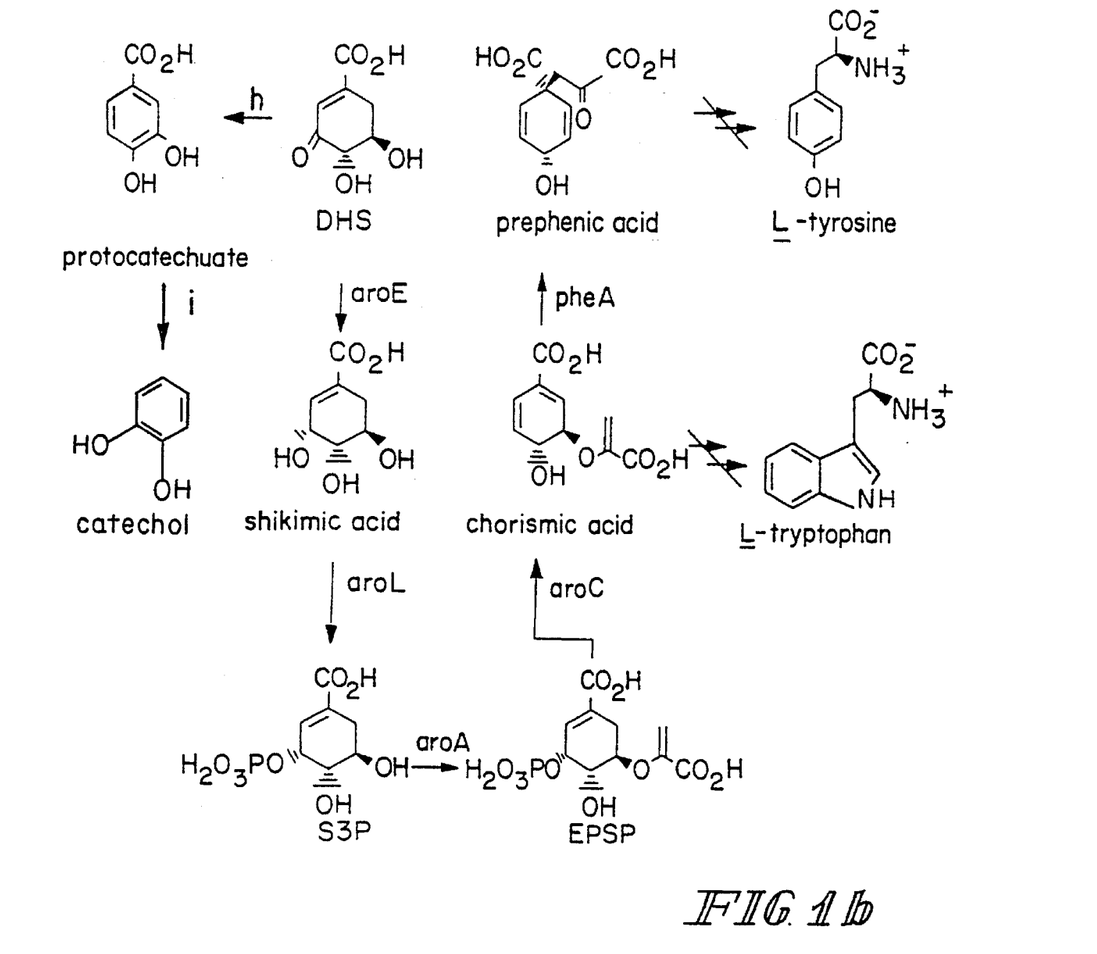

Biomass-derived carbon sources useable in accordance with this invention include any carbon sources capable of being biocatalytically converted into D-erythrose 4-phosphate (E4P) and phosphoenolpyruvate (PEP), two precursor compounds to the common pathway of aromatic amino acid biosynthesis (see FIG. 1). Suitable carbon sources include, but are not limited to, starches, cellulose, and sugar moieties such as glucose, pentoses, and fructose. In preferred embodiments, D-glucose is the carbon source for use by host cells in accordance with the present invention.

Host cells suitable for use in the present invention are members of those genera capable of being utilized for industrial biosynthetic production of desired aromatic compounds. In particular, suitable host cells have an endogenous common pathway of aromatic amino acid biosynthesis. Common aromatic pathways are endogenous in a wide variety of microorganisms, and are used for the production of various aromatic compounds. As illustrated in FIG. 1, the common aromatic pathway leads from E4P and PEP (the availability of E4P being increased by the pentose phosphate pathway enzyme transketolase, encoded by the tkt gene) to chorismic acid with many intermediates in the pathway. The intermediates in the pathway include 3-deoxy-D-arabino-heptulosonic acid 7-phosphate (DAHP), 3-dehydroquinate (DHQ), 3-dehydroshikimate (DHS), shikimic acid, shikimate 3-phosphate (S3P), and 5-enolpyruvoylshikimate-3-phosphate (EPSP). The enzymes in the common pathway, and their respective genes, include DAHP synthase (aroF), DHQ synthase (aroB), DHQ dehydratase (aroD), shikimate dehydrogenase (aroE), shikimate kinase (aroL, aroK), EPSP synthase (aroA) and chorismate synthase (aroC).

Host cells including common pathways of this type include prokaryotes belonging to the genera Escherichia, Klebsiella, Corynebacterium, Brevibacterium, Arthrobacter, Bacillus, Pseudomonas, Streptomyces, Staphylococcus, or Serratia. Eukaryotic host cells can also be utilized, with yeasts of the genus Saccharomyces or Schizosaccharomyces being preferred.

More specifically, prokaryotic host cells are derived from species that include *Escherichia coli, Klebsiella pneumonia, Corynebacterium glutamicum, Corynebacterium herculis, Brevibacterium divaricatum, Brevibacterium lactofermentum, Brevibacterium flavum, Bacillus brevis, Bacillus cereus, Bacillus circulans, Bacillus coagulans, Bacillus lichenformis, Bacillus megaterium, Bacillus mesentericus, Bacillus pumilis, Bacillus subtilis, Pseudomonas aeruginosa, Pseudomonas angulata, Pseudomonas fluorescens, Pseudomonas tabaci, Streptomyces aureofaciens, Streptomyces avermitilis, Streptomyces coelicolor, Streptomyces griseus, Streptomyces kasugensis, Streptomyces lavendulae, Streptomyces lipmanii, Streptomyces lividans, Staphylococcus epidermis, Staphylococcus saprophyticus,* or *Serratia marcescens.* Preferred eukaryotic host cells include *Saccharomyces cerevisiae* or *Saccharomyces carlsbergensis.*

In preferred embodiments of the invention, host cells include auxotrophic mutant cell lines having a mutation that blocks the conversion of DHS to the branch point molecule, chorismate. Such mutants are unable to catalyze the conversion of 3-dehydroshikimate (DHS) into chorismate due to a mutation in one or more of the genes encoding shikimate dehydrogenase, shikimate kinase, EPSP synthase and chorismate synthase, and will thus accumulate elevated intracellular levels of DHS. Preferred mutant cell lines include *Escherichia coli* strains AB2834, AB2829 and AB2849.

*E. coli* AB2834 is unable to catalyze the conversion of 3-dehydroshikimate (DHS) into shikimic acid due to a mutation in the aroE locus which encodes shikimate dehydrogenase. Use of *E. coli* AB2834 ensures that the carbon flow directed into aromatic amino acid biosynthesis is not processed beyond DHS. Similarly *E. coli* AB2829 (which is unable to catalyze the conversion of shikimate 3-phosphate (S3P) into 5-enolpyruvylshikimate- 3-phosphate (EPSP) due to a mutation in the aroA locus which encodes EPSP synthase) and *E. coli* AB2849 (which is unable to catalyze the conversion of EPSP into chorismic acid due to a mutation in the aroC locus which encodes chorismate synthase) also result in increased intracellular levels of DHS. *E. coli* AB2834 is the host cell line used in preferred embodiments.

To be used according to the present invention, host cells of the type described herein are transformed so that the intracellular DHS can be used as a substrate for biocatalytic conversion to catechol, which can thereafter be converted to adipic acid. Preferably, host cells are transformed with recombinant DNA to force carbon flow away from the common pathway of aromatic amino acid biosynthesis after DHS is produced and into a divergent pathway to produce adipic acid.

The divergent pathway is illustrated in FIG. 1. As shown, the intermediates in the divergent pathway are protocatechuate, catechol, and cis, cis-muconic acid. The enzyme responsible for the biocatalytic conversion of DHS to protocatechuate is the enzyme 3-dehydroshikimate dehydratase, labelled "h" in FIG. 1, and its gene is aroZ. The enzyme responsible for the decarboxylation of protocatechuate to form catechol is protocatechuate decarboxylase, labelled "i" in FIG. 1, and its gene is aroY. Lastly, the enzyme catalyzing the oxidation of catechol to produce cis, cis-muconic acid is catechol 1,2-dioxygenase (see "j" in FIG. 1). Its gene is catA. The cis, cis-muconic acid is thereafter hydrogenated to produc adipic acid as indicated by the label "k" in FIG. 1. Thus, the recombinantly transformed host cells for use in accordance with the present invention are preferably characterized by the constitutive expression of structural genes encoding 3-dehydroshikimate dehydratase, protocatechuate decarboxylase, and catechol 1,2-dioxygenase.

The enzymes 3-dehydroshikimate dehydratase and protocatechuate decarboxylase are recruited from the ortho cleavage pathways which enable microbes such as Neurospora, Aspergillus, Acinetobacter, Klebsiella, and Pseudomonas to use aromatics (benzoate and p-hydroxybenzoate) as well as hydroaromatics (shikimate and quinate) as sole sources of carbon for growth. DHS dehydratase plays a critical role in microbial catabolism of quinic and shikimic acid. Protocatechuate decarboxylase was formulated by Patel to catalyze the conversion of protocatechuate into catechol during catabolism of p-hydroxybenzoate by *Klebsiella aerogenes*. Reexamination of Patel's strain (now referred to as *Enterobacter aerogenes*) [(a) Grant, D. J. W.; Patel, J. C. *Antonie van Leewenhoek* 1969, 35, 325. (b) Grant, D. J. W. *Antonie van Leewenhoek* 1970, 36, 161] recently led Ornston to conclude that protocatechuate decarboxylase was not metabolically significant in catabolism of p-hydroxybenzoate [Doten, R. C.; Ornston, N. *J. Bacteriol.* 1987, 169, 5827]. The true role of protocatechuate decarboxylase in ortho cleavage is thus something of an enigma.

The mechanism for transforming the host cell to direct carbon flow into the divergent pathway preferably involves the insertion of genetic elements including expressible sequences coding for 3-dehydroshikimate dehydratase, protocatechuate decarboxylase, and catechol 1,2-dioxygenase. Regardless of the exact mechanism utilized, it is contemplated that the expression of these enzymatic activities will be effected or mediated by the transfer of recombinant genetic elements into the host cell. Genetic elements as herein defined include nucleic acids (generally DNA or RNA) having expressible coding sequences for products such as proteins, apoproteins, or antisense RNA, which can perform or control pathway enzymatic functions. The expressed proteins can function as enzymes, repress or derepress enzyme activity, or control expression of enzymes. The nucleic acids coding these expressible sequences can be either chromosomal (e.g. integrated into a host cell chromosome by homologous recombination) or extrachromosomal (e.g. carried by plasmids, cosmids, etc).

The genetic elements of the present invention can be introduced into a host cell by plasmids, cosmids, phages, yeast artificial chromosomes or other vectors that mediate transfer of the genetic elements into a host cell. These vectors can include an origin of replication along with cis-acting control elements that control replication of the vector and the genetic elements carried by the vector. Selectable markers can be present on the vector to aid in the identification of host cells into which the genetic elements have been introduced. For example, selectable markers can be genes that confer resistance to particular antibiotics such as tetracycline, ampicillin, chloramphenicol, kanamycin, or neomycin.

A preferred means for introducing genetic elements into a host cell utilizes an extrachromosomal multi-copy plasmid vector into which genetic elements in accordance with the present invention are inserted. Plasmid borne introduction of the genetic element into host cells involves an initial cleaving of a plasmid with a restriction enzyme, followed by ligation of the plasmid and genetic elements in accordance with the invention. Upon recircularization of the ligated recombinant plasmid, transduction or other mechanism (e.g., electroporation, microinjection, etc.) for plasmid transfer is utilized to transfer the plasmid into the host cell. Plasmids suitable for insertion of genetic elements into the host cell include but are not limited to pBR322, and its derivatives such as pAT153, pXf3, pBR325, pBr327, pUC vectors, pACYC and its derivatives, pSC101 and its derivatives, and ColE1. In addition cosmid vectors such as pLAFR3 are also suitable for the insertion of genetic elements into host cells. Preferred plasmid constructs include but are not limited to p2-47, pKD8.243A, pKD8.243B, and pSUaroZY157-27, which carry the aroZ and aroY loci isolated from *Klebsiella pneumoniae* which respectively encode 3-dehydroshikimate dehydratase and protocatechuate decarboxylase. Further plasmid constructs preferably used in connection with the present invention include pKD8.292, which carries genetic fragments endogenous to *Acinetobacter calcoaceticus* catA, encoding catechol 1,2-dioxygenase.

Typically, the mechanism for transforming host cells in accordance with the present invention will also include insertion of genes encoding for enzymes which increase commitment of carbon into the common pathway of aromatic amino acid biosynthesis. The expression of a gene is primarily directed by its own promoter, although other genetic elements including optional expression control sequences such as repressors, and enhancers can be included to control expression or derepression of coding sequences for proteins, apoproteins, or antisense RNA. In addition, recombinant DNA constructs can be generated whereby the gene's natural promoter is replaced with an alternative promoter to increase expression of the gene product. Promoters can be either constitutive or inducible. A constitutive promoter controls transcription of a gene at a constant rate during the life of a cell, whereas an inducible promoter's activity fluctuates as determined by the presence (or absence) of a specific inducer. For example, control sequences can be inserted into wild type host cells to promote overexpression of selected enzymes already encoded in the host cell genome, or alternatively can be used to control synthesis of extrachromosomally encoded enzymes.

In the present invention, control sequences to promote overproduction of DHS are preferably used. As previously noted, DHS is synthesized in the common pathway by the sequential catalytic activities of the tyrosine-sensitive isozyme of 3-deoxy-D-arabino-heptulosonic acid 7-phosphate (DAHP) synthase (encoded by aroF) and 3-dehydroquinate (DHQ) synthase (encoded by aroB) along with the pentose phosphate pathway enzyme transketolase (encoded by tkt). The expression of these biosynthetic enzymes can be amplified to increase the conversion of D-glucose into DHS. Increasing the in vivo catalytic activity of DAHP synthase, the first enzyme of the common pathway, increases the flow of D-glucose equivalents directed into aromatic biosynthesis. However, levels of DAHP synthase catalytic activity are reached beyond which no further improvements are achieved in the percentage of D-glucose which is committed to aromatic biosynthesis. At this limiting level of aromatic amino acid biosynthesis, amplification of the catalytic levels of the pentose phosphate pathway enzyme transketolase achieves sizable increases in the percentage of D-glucose siphoned into the pathway.

Amplified transketolase activity has been suggested to increase D-erythrose 4-phosphate concentrations. As one of the two substrates for DAHP synthase, limited D-erythrose 4-phosphate availability likely limits DAHP synthase catalytic activity. One preferred means of amplifying the catalytic activities of DAHP synthase, DHQ synthase and DHQ dehydratase is to overexpress the enzyme species by transforming the microbial catalyst with a recombinant DNA sequence encoding these enzymes.

Amplified expression of aroF-encoded DAHP synthase and tkt-encoded transketolase creates a surge of carbon flow directed into the common pathway of aromatic amino acid biosynthesis which is in excess of the normal carbon flow directed into this pathway. If the individual rates of conversion of substrate into product catalyzed by individual common pathway enzymes are not similar to the rate of DAHP synthesis, the substrates of these rate-limiting enzymes will accumulate intracellularly.

Microbial organisms such as *E. coli* frequently cope with accumulated substrates by exporting such substrates into the growth supernatant. This results in a loss of carbon flow through the common pathway since exported substrates are typically lost to the microbe's metabolism. DHQ synthase is a example of a rate-limiting common pathway enzyme. Amplified expression of DHQ synthase removes the rate-limiting character of this enzyme, and prevents the accumulation of DAHP and its nonphosphorylated analog, DAH. DHQ dehydratase is not rate-limiting. Therefore, amplified expression of aroF-encoded DAHP synthase, tkt-encoded transketolase and aroB-DHQ synthase increases production of DHS, which in the presence of DHS dehydratase and protocatechuate decarboxylase is converted to catechol, which is subsequently biocatalytically converted to cis, cis-muconic acid, and thereafter to adipic acid.

One particularly preferred plasmid for promoting the efficiency of carbon flow along the common pathway between the carbon source and DHS is plasmid pKD136, which encodes the aroF, tkt and aroB genes. Plasmid pKD136 directs the surge of carbon flow into aromatic biosynthesis due to amplified expression of DAHP synthase (encoded by aroF) and transketolase (encoded by tkt). This surge of carbon flow is then delivered intact into DHS synthesis by pKD136 due to amplified expression of DHQ synthase (encoded by aroB).

Thus, in accordance with one preferred embodiment of the present invention, a heterologous strain of *Escherichia coli* expressing genes encoding DHS dehydratase, protocatechuate decarboxylase, and catechol 1,2-dioxygenase has been constructed enabling the biocatalytic conversion of D-glucose to cis, cis-muconic acid, which is then hydrogenated to afford adipic acid. Efficient conversion of D-glucose to DHS was accomplished upon transformation of the host cell with pKD136. The strain *E. coli* AB2834/pKD136 was then transformed with plasmids pKD8.243A and pKD8.292. The end result was *E. coli* AB2834/pKD136/pKD8.243A/pKD8.292 which expresses the enzyme species 3-dehydroshikimate dehydratase, protocatechuate decarboxylase and catechol 1,2,-dioxygenase. This bacterial cell line was deposited with the American Type Culture Collection, 12301 Parklawn Drive, Rockville Md. 20852, on Aug. 1, 1995 and assigned accession number 69875. In another preferred embodiment, *E. coli* AB2834/pKD136 is transformed with plasmids p2-47 and pKD8.292 to generate *E. coli* AB2834/pKD136/p2-47/pKD8.292. In a further preferred embodiment *E. coli* AB2834/pKD136 is transformed with plasmids pKD8.243B and pKD8.292 to generate *E. coli* AB2834/pKD136/p2-47/pKD8.292. Each of these heterologous host cell lines catalyzes the conversion of D-glucose into cis, cis-muconic acid. Synthesized cis, cis-muconic acid accumulates extracellularly and can be separated from the cells by centrifugation. Direct hydrogenation of the culture supernatant over 10% platinum at 50 psi hydrogen pressure provides a 90% conversion of cis, cis-muconic acid into adipic acid.

The present invention thus relates to a transformant of a host cell having an endogenous common pathway of aromatic amino acid biosynthesis. The transformant is characterized by the constitutive expression of heterologous structural genes encoding 3-dehydroshikimate dehydratase, protocatechuate decarboxylase, and catechol 1,2-dioxygenase. In one preferred aspect of the invention, the cell transformant is further transformed with expressible recombinant DNA sequences encoding the enzymes transketolase, DAHP synthase, and DHQ synthase. In another preferred aspect, the host cell is selected from the group of mutant cell lines including mutations having a mutation in the common pathway of amino acid biosynthesis that blocks the conversion of 3-dehydroshikimate to chorismate. In yet a further preferred aspect, the structural genes encoding 3-dehydroshikimate dehydratase and protocatechuate decarboxylase are endogenous to *Klebsiella pneumoniae*. In yet a further preferred aspect, the heterologous structural genes encoding catechol 1,2-dioxygenase are endogenous to *Acinetobacter calcoaceticus*.

In another preferred embodiment of the present invention, a method is provided for producing adipic acid. The method comprises the steps of culturing a transformed host cell of the type described above in a medium containing a carbon source capable of being converted to 3-dehydroshikimate by the enzymes in the common pathway of aromatic amino acid biosynthesis of said cell to produce cis, cis-muconic acid by the biocatalytic conversion of 3-dehydroshikimate, and reducing the cis, cis-muconic acid to produce adipic acid.

In yet another preferred embodiment, a method is provided for producing a cell transformant capable of biocatalytically converting a biomass-derived carbon source to cis, cis-muconic acid. The method comprises the steps of transforming a host cell having an endogenous common pathway of aromatic amino acid biosynthesis with recombinant DNA to create a heterologous host cell, said DNA comprising constitutively expressed genes encoding 3-dehydroshikimate dehydratase, protocatechuate decarboxylase, and catechol 1,2-dioxygenase. In yet another embodiment, a method is provided for producing adipic acid, the method comprising the steps of culturing the transformant in accordance with the method described above under conditions enabling conversion of a carbon source to cis, cis-muconic acid, and hydrogenating the cis, cis-muconic acid to produce adipic acid.

In yet a further embodiment of the invention, a method is provided for producing adipic acid which comprises the steps of culturing a cell transformant capable of converting a carbon source to catechol for a period of time sufficient to convert said carbon source to catechol, biocatalytically converting the catechol to cis, cis-muconic acid using catechol 1,2-dioxygenase, and hydrogenating the cis, cis-muconic acid to produce adipic acid.

EXAMPLE 1

Cloning of the aroZ Gene

The gene which encodes DHS dehydratase, designated aroZ, was isolated from a genomic library of *Klebsiella pneumoniae* DNA. Genomic DNA was purified from *K. pneumoniae* strain A170-40 and partially digested with BamH I to produce fragments in the range of 15 kb to 30 kb. The resulting DNA fragments were ligated to cosmid pLAFR3 which had previously been digested with BamH I and subsequently treated with calf intestinal alkaline phosphatase. pLAFR3 is a tetracycline resistant cosmid possessing the RK2 replicon. Ligated DNA was packaged using Packagene Packaging System (Promega), and the resulting phage particles were used to infect *E. coli* DH5α/pKD136. Plasmid pKD136 is a pBR325-based vector (pMB1 origin of replication) containing genes which encode transketolase (tkt), DAHP synthase (aroF), and DHQ synthase (aroB) as well as an ampicillin resistance gene. Colonies which were resistant to both tetracycline and ampicillin were subsequently plated onto chromogenic minimal medium (M9) plates containing D-glucose (4 g L), shikimic acid (0.04 g L), ferric citrate (0.07 g L), p-toluidine (1.9 g L), ampicillin (0.05 g L), and tetracycline (0.013 g L). After incubation at 37° C. for 48 h, the growth medium surrounding colony 5-87 appeared brown in color, analogous to the darkening of the medium which occurred when protocatechuic acid was spotted onto the plate. DNA was purified from a culture of colony 5-87 and consisted of pKD136 and a tetracycline resistant cosmid referred to as p5-87. Cosmid p5-87 contained a 14 kb BamH I fragment which when digested to completion with BamH I produced four detectable fragments of DNA.

EXAMPLE 2

Confirmation of the Cloning of the aroZ Gene

Confirmation that cosmid p5-87 contained the aroZ gene relied on the fact that transformation of an *E. coli* strain which typically converts D-glucose into DHS could further convert DHS into protocatechuic acid. *E. coli* AB2834 accumulates DHS in the culture supernatant due to a mutation in the aroE gene, which encodes shikimate dehydrogenase. Conversion of D-glucose to DHS is maximized when AB2834 is transformed with pKD136. AB2834 was co-transformed with pKD136 and p5-87 to produce colonies which were resistant to both ampicillin and tetracycline. One liter of LB medium (4 L Erlenmeyer flask) was inoculated with an overnight culture (5 mL) of AB2834/pKD136/p5-87. The culture was grown at 37° C. for 8 h with agitation (250 rpm). The cells were then harvested and resuspended in one liter (4 L Erlenmeyer flask) of minimal M9 medium containing glucose (10 g L), shikimic acid (0.04 g L), ampicillin (0.05 g L), and tetracycline (0.013 g L). The culture was returned to 37° C. incubation. Aliquots of the culture were removed after 24 h and 64 h and centrifuged to remove cells. Five milliliters of isolated supernatant was collected from each sample and the water was removed in vacuo. Samples were redissolved in $D_2O$ and concentrated in vacuo. Repetition of this procedure resulted in exchange of residual water with $D_2O$ and samples suitable for analysis by H NMR. Using the sodium salt of 3-(trimethylsilyl)propionic-2,2,3,3-$d_4$ acid as an internal standard, it was determined that approximately 9 mM protocatechuic acid had accumulated in the culture supernatant. Diagnostic resonances at $\delta 6.94$ (d, 7 Hz, 1H) and $\delta 7.48$ (d, 7 Hz, 2H) were indicative of protocatechuic acid. DHS was not detected in the culture supernatant. It was concluded from this experiment that the gene which encodes DHS dehydratase was localized on plasmid p5-87.

EXAMPLE 3

Subcloning of the aroZ Gene

In an effort to minimize the size of the aroZ-encoding insert plasmid p5-87 was digested with BamH I and the resulting fragments were ligated to vector pSU19 which had previously been digested with BamH I and treated with phosphatase. Plasmid pSU19 contains the p15A replicon and the gene which imparts resistance to chloramphenicol. Following transformation of the ligation products into *E. coli* DH5 α/pKD136, the resulting ampicillin and chloramphenicol resistant colonies were screened as described in Example 1 for the ability to turn chromogenic minimal medium agarose plates containing p-toluidine and ferric citrate brown. Using this technique, plasmid pSU1-31 was isolated which consisted of a 3.5 kb BamH I insert contained in pSU19. When AB2834/pKD136/pSU1-31 was grown on a 1 L scale under conditions similar to those described in Example 1, H NMR analysis of the culture supernatant of indicated that 11 mM protocatechuic acid accumulated extracellularly.

EXAMPLE 4

Cloning of the aroY Gene

A fragment of DNA containing the aroY gene was isolated based on the fact that a strain which normally synthesizes protocatechuate will instead synthesize catechol in the presence of catalytically active protocatechuate decarboxylase. Cosmid p4-20 was prepared which contained the 3.5 kb BamH I aroZ fragment localized in pLAFR3. A library of *Klebsiella pneumoniae* DNA digested with EcoR I was prepared in cosmid p4-20 analogous to what had been constructed earlier in pLAFR3. DNA packaged in lambda phage heads was used to infect *E. coli* DH5α/pKD136, resulting in colonies resistant to both ampicillin and tetracycline. Colonies were screened on chromogenic minimal medium agarose plates containing p-toluidine and ferric citrate. Since addition of catechol to chromogenic minimal medium gives rise to a more intense darkening of the surrounding agarose than does addition of an equal quantity of protocatechuic acid, it was expected that those colonies synthesizing catechol could be selected from a background of colonies synthesizing protocatechuate. After incubation at 37° C. for approximately 24 h, colony 2-47 was producing a local region of brown that was lacking from all other colonies.

Isolation of DNA from colony 2-47 yielded plasmid pKD136 and plasmid p2-47 which were subsequently co-transformed into competent cells to yield *E. coli* AB2834/pKD136/p2-47. The culture supernatant of AB2834/pKD136/p2-47 was analyzed by $^1$H NMR as described in Example 2. After 48 h in minimal medium, a solution of 56 mM D-glucose was converted to a solution of 20 mM catechol by AB2834/pKD136/p2-47.

EXAMPLE 5

Subcloning of the aroY Gene

Figure 2:
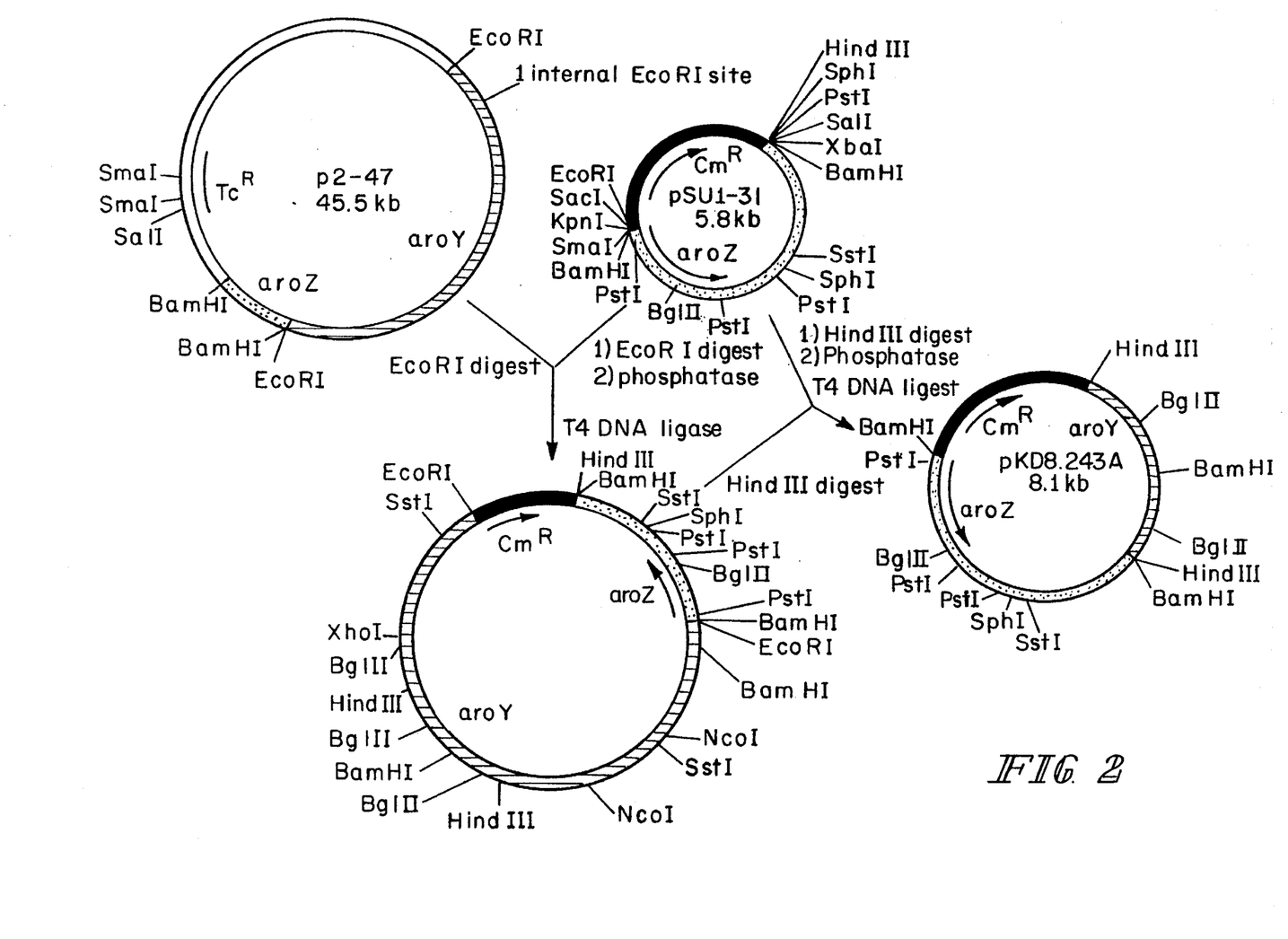
FIG. 2 presents a plasmid map of p2-47 and illustrates how plasmid pKD8.243A was generated from plasmids p2-47, pSU1-31, and pSUaroZY 157-27; and, FIG. 3 presents a plasmid map of pKD8.292 and illustrates how plasmid pKD8.292 was generated from plasmids pIB1345 and pCL1920.

Similar to the original strategy for isolation of the DNA encoding protocatechuate decarboxylase, subcloning of the aroY EcoR I fragment to its minimal size also relied on synthesis of catechol by an aroE host strain in the presence of DHS dehydratase. Digestion of p2-47 to completion with EcoR I indicated that the aroY insert consisted of two EcoR I fragments of approximately 8 kb and 11.9 kb. Localization of the 11.9 kb EcoR I fragment in pSU1-31 yielded plasmid pSUaroZY157-27. When grown on a 1 L scale under conditions similar to those described in Example 2, *E. coli* AB2834/pKD136/pSUaroZY157-27 accumulated 16 mM catechol in the culture supernatant when supplied with 56 mM D-glucose. Mapping of the 11.9 kb EcoR I fragment in conjunction with further subcloning indicated that the aroY gene was likely located near the middle of the 11.9 kb fragment. Digestion of pSUaroZY157-27 with Hind III produced a 2.3 kb Hind III fragment which was inserted into pSU1-31, yielding plasmid pKD8.243A (FIG. 2). Plasmid pKD8.243B was also isolated in which the 2.3 kb Hind III fragment is in the opposite orientation relative to the vector. Each of these plasmids was co-transformed into AB2834 with plasmid pKD136. When grown on a 1 L scale under conditions similar to those described in Example 2, AB2834/pKD136/pKD8.243A synthesized 16 mM catechol from 56 mM D-glucose within 48 h whereas AB2834/pKD136/pKD8.243B synthesized 10 mM catechol. Protocatechuic acid (<4 mM) was also detected in some of the culture supernatants, though not on a consistent basis and not always at the end of the microbial synthesis.

EXAMPLE 6

Figure 3:
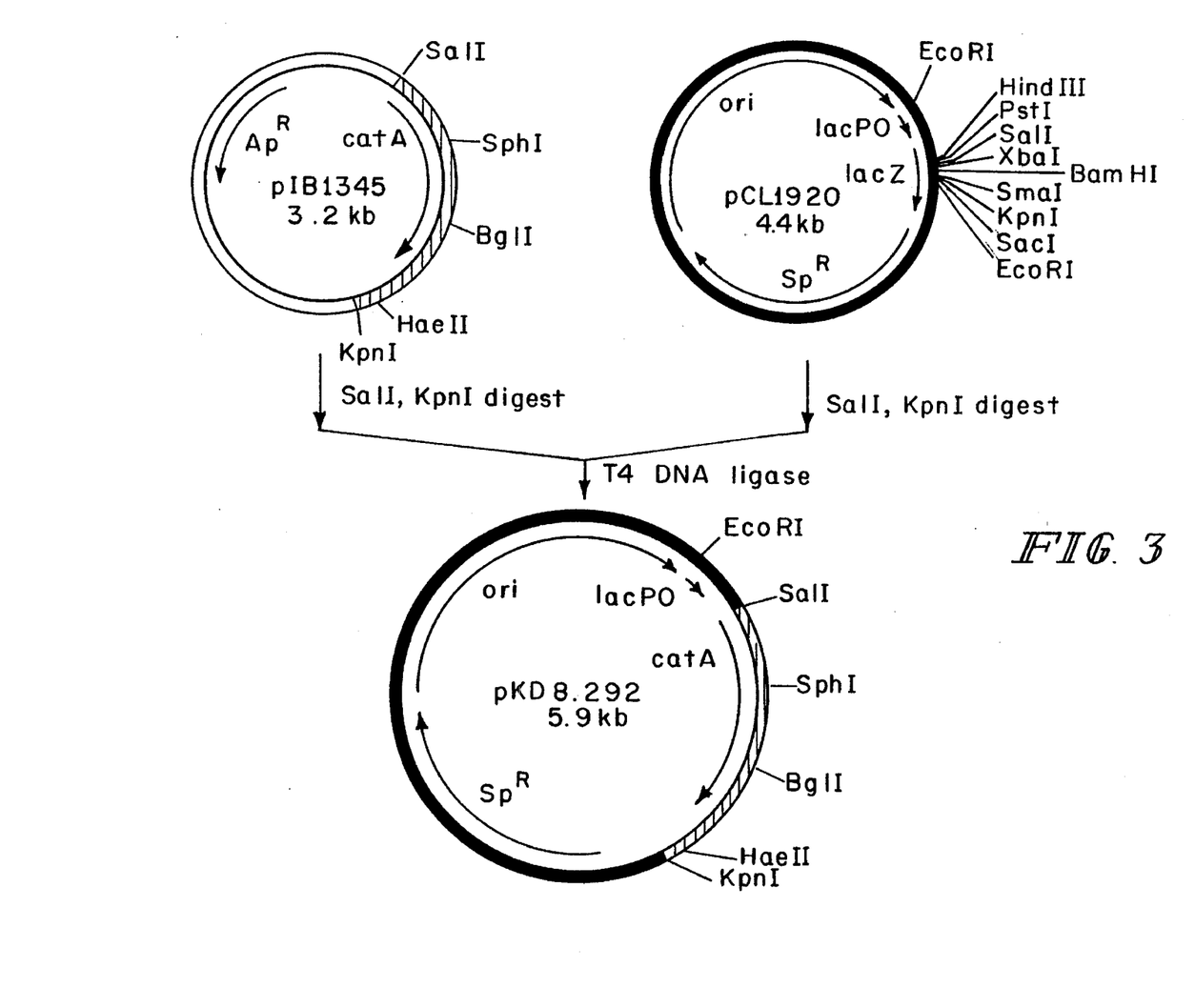

Enzymatic Activities of DHS Dehydratase, Protocatechuate Decarboxylase, and Catechol 1,2-Dioxygenase Expression of catechol 1,2-dioxygenase in an organism capable of catalyzing conversion of D-glucose into catechol was expected to result in microbial synthesis of cis, cis-muconic acid. Plasmid pIB 1345 was obtained which contains the *Acinetobacter calcoaceticus* catA gene expressed from a lac promoter supplied by the host vector pUC19. A three plasmid system was designed for microbial synthesis of cis, cis-muconate from D-glucose. Plasmids pKD136 (pMB1 origin, ampicillin resistance) and pKD8.243A (p15A origin, chloramphenicol resistance) were found to be stably maintained under the growth conditions employed. A third plasmid, pCL1920, was chosen for expression of catechol 1,2-dioxygenase. Plasmid pCL1920 is a low copy vector containing the pSC101 origin of replication and a gene which confers resistance to spectinomycin. Digestion of pIB1345 with Sal I and Kpn I yielded a 1.5 kb fragment which was subsequently localized in pCL1920 to produce pKD8.292 (FIG. 3) in which catechol 1,2-dioxygenase was expressed from the vector-encoded lac promoter. Transformation of AB2834/pKD136 with pKD8.243A and pKD8.292 yielded colonies which were resistant to ampicillin, chloramphenicol, and spectinomycin.

Enzyme activities were determined to confirm that *E. coli* AB2834/pKD136/pKD8.243A/pKD8.292 was expressing each of the genes from the ortho cleavage pathway necessary to convert DHS into cis, cis-muconate. Cultures of AB2834/pKD136/pKD8.243A/pKD8.292 were grown in LB (1 L) containing IPTG (0.2 mM), ampicillin (0.05 g), chloramphenicol (0.02 g) and spectinomycin (0.05 g) for 10 h at 37° C., 250 rpm. Cells were harvested and resuspended in 100 mM Tris HCl, pH 7.5,2.5 mM MgCl$_2$. After two passages through a French pressure cell (16,000 psi), the lysate was clarified by centrifugation (40,000 g, 30 min, 4° C.). To measure DHS dehydratase activity, each assay contained (final volume of 1 mL) 100 mM Tris HCl, pH 7.5, 25 mM MgCl$_2$, 1 mM DHS, and cellular lysate. After addition of DHS, formation of protocatechuate ($\epsilon$=3890 M cm) was monitored at 290 nm for several minutes. DHS dehydratase activity measured for three samples of AB2834/pKD136/pKD8.243A/pKD8.292 was determined to be 0.078 units mg ±0.009, where one unit is the amount of enzyme necessary to convert 1 μmol of DHS to protocatechuic acid in 1 min.

Catechol 1,2-dioxygenase specific activity was determined using the same cellular lysate samples produced above. Each assay contained 100 mM potassium phosphate, pH 7.5,0.2 mM catechol, and cellular lysate. Formation of cis, cis-muconate was monitored by following the increase in absorbance at 260 nm. Assuming a difference in molar extinction coefficient between cis, cis-muconate and catechol to be 16,000M cm under the conditions of the assay, catechol 1,2-dioxygenase activity in AB2834/pKD136/pKD8.243A/pKD8.292 was determined to be 0.25 units mg ±0.03, where one unit corresponds to the formation of 1 μmol of cis, cis-muconate per min.

To determine the activity of protocatechuate decarboxylase, AB2834/pKD136/pKD8.243A/pKD8.292 was grown as described previously in Example 6. Cells were harvested and resuspended in 75 mM phosphate buffer, pH 7.1. Following disruption by passage through a French pressure cell (16,000 psi), the lysate was clarified by centrifugation (40,000 g, 30 min, 4° C.). Protocatechuate decarboxylase activity was determined by following the consumption of protocatechuic acid. Each assay (final volume of 1 mL) contained 75 mM sodium phosphate, pH 6.0,0.3 mM protocatechuic acid, and cellular lysate. The loss of absorbance at 290 nm was monitored over time. Protocatechuate decarboxylase activity in AB2834/pKD136/pKD8.243A/pKD8.292 was determined to be 0.028 units mg ±0.009, where one unit corresponds to the oxidation of 1 μmol of protocatechuic acid per min.

EXAMPLE 7

Conversion of D-glucose to Cis, Cis-Muconate

Microbial synthesis of cis, cis-muconate from D-glucose utilizing *E. coli* AB2834/pKD136/pKD8.243A/pKD8.292 proceeded as follows. One liter of LB medium (in 4 L Erlenmeyer shake flask) containing IPTG (0.2 mM), ampicillin (0.05 g), chloramphenicol (0.02 g) and spectinomycin (0.05 g) was inoculated with 10 mL of an overnight culture of AB2834/pKD136/pKD8.243A/pKD8.292. Cells were grown at 250 rpm for 10 h at 37° C. The cells were harvested, resuspended in 1 L of M9 minimal medium containing 56 mM D-glucose, shikimic acid (0.04 g), IPTG (0.2 mM), ampicillin (0.05 g), chloramphenicol (0.02 g) and spectinomycin (0.05 g). The cultures were returned to 37° C. incubation. After resuspension in minimal medium the pH of the culture was closely monitored, particularly over the initial 12 h. When the culture reached a pH of 6.5, 5N NaOH was added to adjust the pH back to approximately 6.8. Over the 48 h accumulation period, the culture was not allowed to fall below pH 6.3. After 24 h in minimal medium 12 mM cis, cis-muconate and 1 mM protocatechuate were detected, using methods described in Example 2, in the culture supernatant along with 23 mM D-glucose. After 48 h in minimal medium AB2834/pKD136/pKD8.243A/pKD8.292 had replaced the 56 mM D-glucose with 17 mM cis, cis-muconate.

Experiments were also conducted in which the pH of the culture supernatant was not adjusted over time in minimal medium. In this case, after the initial 24 h in minimal medium the solution had dropped to approximately pH 5. A mixture of cis, cis-muconate and cis, trans-muconate was detected using methods described in Example 2, in the medium which totaled 13 mM muconate. D-glucose (32 mM) was also detected in the culture supernatant. Additional incubation of the culture at 37° C. failed to result in a significant increase in muconate synthesis, although by 48 h all of the synthesized muconate had isomerized to the cis, trans isomer.

The reduction of microbially synthesized cis, cis-muconate adipic acid proceeded as follows. Fifty milligrams of platinum on carbon (10%) was added to 6 mL of a cell-free culture supernatant of AB2834/pKD136/pKD8.243A/pKD8.292 which contained 17.2 mM cis, cis-muconate. The sample was hydrogenated at 50 psi hydrogen pressure for 3 h at room temperature. After filtration through Celite to remove the catalyst, an aliquot of the solution was concentrated to dryness in vacuo and subsequently concentrated in vacuo from several portions of $D_2O$. The sample was prepared for $^1H$ NMR analysis in a manner analogous to preparation of the untreated cell-free culture supernatant. $^1H$ NMR indicated that the solution contained 15.1 mM adipic acid (90% conversion). No unreacted cis, cis-muconate was detected in the solution.

Although the invention has been described in detail with reference to certain preferred embodiments, variations and modifications exist within the scope and spirit of the invention as described and defined in the following claims.

We claim:

1. A method for producing adipic acid, said method comprising the steps of culturing a bacterial cell, transformed with structural genes from *Klebsiella pneumoniae* which express the enzyme species 3-dehydroshikimate dehydratase and protocatechuate decarboxylase, and a structural gene from *Acinetobacter calcoaceticus* which expresses the enzyme species catechol 1,2-dioxygenase, in a medium containing a carbon source which is converted to 3-dehydroshikimate by the enzymes in the common pathway of aromatic amino acid biosynthesis of said cell, to produce cis, cis-muconic acid at a rate greater than 0.35 millimoles/liter/hour, by the biocatalytic conversion of 3-dehydroshikimate, and reducing the cis, cis-muconic acid to produce adipic acid.

2. A method for producing adipic acid, said method comprising the steps of culturing a transformed bacterial cell, which expresses heterologous structural genes encoding 3-dehydroshikimate dehydratase, protocatechuate decarboxylase, catechol 1,2-dioxygenase, transketolase, 3-deoxy-D-arabino-heptulosonate 7-phosphate synthase, and 3-dehydroquinate synthase, in a medium containing a carbon source which is converted to 3-dehydroshikimate, by the enzymes in the common pathway of aromatic amino acid biosynthesis of said cell, to produce cis, cis-muconic acid at a rate greater than 0.35 millimoles/liter/hour by the biocatalytic conversion of 3-dehydroshikimate, and reducing the cis, cis-muconic acid to produce adipic acid.

3. A method for producing adipic acid, the method comprising the steps of culturing a bacterial cell, transformed with structural genes from *Klebsiella pneumoniae* which express the enzyme species 3-dehydroshikimate dehydratase and protocatechuate decarboxylase and a structural gene from *Acinetobacter calcoaceticus* which expresses the enzyme catechol 1,2-dioxygenase in a medium containing a carbon source, under conditions in which the carbon source is biocatalytically converted to cis, cis-muconic acid at a rate greater than 0.35 millimoles/liter/hour, and hydrogenating the cis, cis-muconic acid to produce adipic acid.

* * * * *